United States Patent
Haddadi et al.

(10) Patent No.: US 9,974,435 B2
(45) Date of Patent: May 22, 2018

(54) QUALITY CONTROL METHOD FOR OPTOMETRIC MEASUREMENTS

(71) Applicant: ESSILOR INTERNATIONAL (COMPAGNIE GENERALE D'OPTIQUE), Charenton-le-pont (FR)

(72) Inventors: Ahmed Haddadi, Charenton-le-pont (FR); Marie-Anne Berthezene, Charenton-le-pont (FR); Isabelle Poulain, Charenton-le-pont (FR); Cecile Petignaud, Charenton-le-pont (FR); Loic Levraud, Charenton-le-pont (FR); Sebastien Gayat, Charenton-le-pont (FR); Fabien Divo, Charenton-le-pont (FR); Benjamin Rousseau, Charenton-le-pont (FR)

(73) Assignee: ESSILOR INTERNATIONAL (COMPAGNIE GENERAL D'OPTIQUE), Charenton-le-Pont (FR)

( * ) Notice: Subject to any disclaimer, the term of this patent is extended or adjusted under 35 U.S.C. 154(b) by 51 days.

(21) Appl. No.: 15/034,301

(22) PCT Filed: Oct. 17, 2014

(86) PCT No.: PCT/FR2014/052652
§ 371 (c)(1),
(2) Date: May 4, 2016

(87) PCT Pub. No.: WO2015/067870
PCT Pub. Date: May 14, 2015

(65) Prior Publication Data
US 2016/0353985 A1 Dec. 8, 2016

(30) Foreign Application Priority Data
Nov. 8, 2013 (FR) ..................................... 13 60989

(51) Int. Cl.
*A61B 3/00* (2006.01)
*A61B 3/103* (2006.01)
(Continued)

(52) U.S. Cl.
CPC .......... *A61B 3/0066* (2013.01); *A61B 3/0025* (2013.01); *A61B 3/103* (2013.01);
(Continued)

(58) Field of Classification Search
CPC ... A61B 3/0066; A61B 3/0025; A61B 3/0041; A61B 3/10; A61B 3/103; A61B 3/11; A61B 5/0022; G02C 13/005; G06F 19/322
(Continued)

(56) References Cited

U.S. PATENT DOCUMENTS 5,903,334 A * 5/1999 Sakurai ............... A61B 3/0066
351/200
9,411,936 B2 * 8/2016 Landrum ............. A61B 5/0006
(Continued)

FOREIGN PATENT DOCUMENTS

EP 2 385 474 A1 11/2011
EP 2 466 540 A1 6/2012
EP 2 600 157 A1 6/2013

OTHER PUBLICATIONS

International Search Report, dated Dec. 22, 2014, from corresponding PCT Application.

*Primary Examiner* — Jordan Schwartz
(74) *Attorney, Agent, or Firm* — Young & Thompson

(57) ABSTRACT

A quality control method for optometric measurements includes the following steps: (a) recording, via computer, a first record (14) that includes at least one first value of a first identifier (12), enabling identification of a glasses wearer (1), and at least one other value of another identifier (13)
(Continued)

Figure 1:
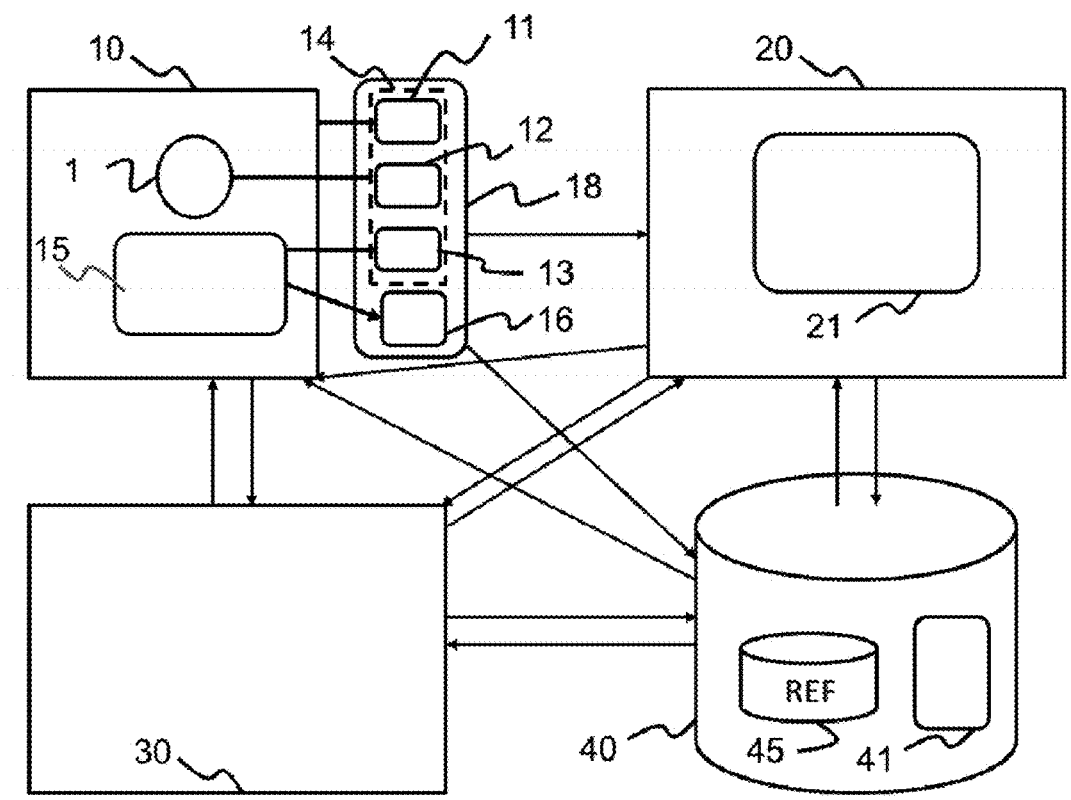

enabling identification of an optometric apparatus (15) on a first optometric measuring site (10); (b) carrying out at least one optometric measurement (16) of the wearer; (c) sending, to a second site (20), a digital measurement data set (18) including the optometric measurement result from step (b), the digital data set being linked, via computer, to the first record; and (d) digitally processing the optometric measurement result from the first record (14) on the basis of a digital data reference system (45) and the values of the respective identifiers of the glasses wearer and the optometric apparatus of the first record.

16 Claims, 3 Drawing Sheets

(51) Int. Cl.
*A61B 3/11* (2006.01)
*G02C 13/00* (2006.01)
*A61B 5/00* (2006.01)
*G06F 19/00* (2018.01)

(52) U.S. Cl.
CPC .............. *A61B 3/11* (2013.01); *A61B 5/0022* (2013.01); *G02C 13/005* (2013.01); *G06F 19/322* (2013.01); *G16H 10/60* (2018.01)

(58) Field of Classification Search
USPC .......................................................... 351/246
See application file for complete search history.

(56) References Cited

U.S. PATENT DOCUMENTS

| | | | |
|---|---|---|---|
| 2007/0123768 A1* | 5/2007 | Freedman | A61B 3/1005 600/405 |
| 2013/0204237 A1* | 8/2013 | Fabrikant | A61B 3/107 606/5 |
| 2013/0231941 A1 | 9/2013 | Pham et al. | |
| 2014/0300860 A1* | 10/2014 | Tanaka | A61B 3/18 351/205 |
| 2015/0342454 A1* | 12/2015 | Foster | A61B 3/103 351/211 |
| 2015/0346512 A1* | 12/2015 | Spratt | G02C 7/027 351/159.76 |
| 2016/0004820 A1* | 1/2016 | Moore | G06F 19/321 705/3 |
| 2016/0183796 A1* | 6/2016 | Fukuma | G06F 19/3418 705/2 |

* cited by examiner

QUALITY CONTROL METHOD FOR OPTOMETRIC MEASUREMENTS

TECHNICAL FIELD TO WHICH THE INVENTION RELATES

The present invention relates generally to the field of the manufacture of ophthalmic compensation lenses fitted in prescription spectacles.

It more particularly relates to a method for controlling the quality of optometric measurements used to determine the optical refraction properties and the quality of ophthalmic lenses suitable for a spectacle wearer.

TECHNOLOGICAL BACKGROUND

Conventionally, the manufacture of ophthalmic compensation lenses requires on the one hand ophthalmic measurements to determine in particular the ocular refraction characteristics of the eyes of a person and on the other hand complementary measurements, especially of geometrico-morphological parameters of the wearer. These various measurements are required to manufacture and fit adequate ophthalmic lenses in the chosen frame and to adjust the spectacles to the sight and morphology of the wearer.

During an oculo-visual examination, an ophthalmologist or an optometrist carries out optometric measurements to evaluate the visual acuity of a person. The ophthalmic measurements may be obtained by various optometric apparatuses, in particular a refractometer for ocular refraction measurements. In the case where a person has a visual acuity defect, the result of an oculo-visual examination is often a prescription for ophthalmic lenses. This prescription generally indicates the refraction correction, often expressed by eye-lens distance, addition, axis and spherical, cylindrical or prismatic power characteristics, etc., required for the manufacture of adequate ophthalmic compensation lenses for each eye of the wearer.

An optometrist or an endorsed professional salesperson such as a dispensing optician effects the distribution, the fitting of the ophthalmic lenses in a spectacle frame and the adjustment of the lenses to the wearer.

For this purpose, the optometrist or the optician carries out a set of complementary optometric measurements relating to a person. The choice of a frame determines the physical dimensions of the lenses. The conditions of use of the spectacles, such as for example in near, far and/or intermediate vision, lead to the choice of parameters for the ophthalmic lenses from a single-vision, multifocal or progressive lens. In addition, various options allow the type and the quality of the ophthalmic lens to be chosen: mineral or organic material, surface (for example antireflection) treatment, photochromic glass, price range, etc.

The optician also determines the geometrico-morphological properties of the wearer, in particular the inter-pupillary distances or even the height of the focal point(s) relative to the lower edge of the frame. Various optometric apparatuses may be used to obtain the optometric measurements relating to the geometrico-morphological properties of the wearer, such as an autorefractometer, a photorefractive apparatus or a measuring column or tablet. Preferably, the optometric apparatuses allow measurements to be obtained in a natural posture that is ergonomic for the wearer and under well determined visual conditions. Advantageously, certain apparatuses allow optometric measurements in a plurality of habitual postures of the wearer corresponding for example to near, far and/or intermediate vision.

In the present document, the expression "optometric measurement" is understood to mean a measurement relating to one or more ophthalmic, in particular ocular refraction, parameters of a wearer, and/or to one or more geometrico-morphological properties of the wearer, in particular inter-pupillary distances or even the height of the visual axes relative to the edge of a frame, the measurement of pantoscopic angles, of eye-glass distance (EGD), of the position of the eye rotation center (ERC), of the face form angle of the frame, or even of behavioral parameters such as the eye-head coefficient, reading distance, the lowering of the gaze during reading, etc.

According to the laws in force in various countries, ophthalmic and geometrico-morphological optometric measurements may be carried out by the same qualified professional or in contrast must be carried out by various professionals each having reserved activities.

Together, the ophthalmic, geometrico-morphological or other optometric measurements allow the refraction of the lenses to be determined and the base curvature of the ophthalmic lenses to be calculated. The precision of the measurements of these geometrico-morphological parameters of the wearer is essential to ensure the ophthalmic compensation lenses once fitted into spectacles are centered relative to the visual axes of the wearer.

The optometrist or optician then validates the initiation of the manufacturing sequence of the ophthalmic spectacle lenses by a manufacturer. After reception of the adequate ophthalmic lenses, the optician fits the ophthalmic lenses into the spectacle frame chosen by the wearer and adjust the spectacles on the face of the wearer.

However, it has been observed that the precision of optometric measurements varies depending on the instruments used, the care taken with the measurements and depending on the respective professional qualifications of the optometrists, opticians or other authorized professionals involved in the various steps. However, the measurement results are generally not transmitted with a margin of error.

In addition, certain optometric measurements or geometrico-morphological parameters do not correspond to a uniform definition. For example, the pantoscopic angle of a lens represents the angle that the general plane of a lens makes relative to the vertical when worn. However, the sign convention of the pantoscopic angle may vary depending on the apparatus or the measurement center. A given pantoscopic angle may thus be evaluated as +8 degrees or −8 degrees. Such measurement differences are thus a source of errors.

Errors in the optical refraction parameters of the ophthalmic lenses, in the geometrico-morphological parameters, in the centering or adjustment of ophthalmic compensation lenses may, in certain cases, generate ocular complications for the wearer, visual discomfort, headaches or nausea and more generally lead to the wearer being unsatisfied with their spectacles.

Furthermore, there is a need for traceability of the optometric measurements in order to allow the quality of the ophthalmic lenses intended for a spectacle wearer to be adapted.

Document US2013/231941 describes an automatic system for distributing ophthalmic spectacles that allows from an image of the patient certain facial measurements to be determined. Document EP 2 466 540 describes a system for supervising and maintaining medical instruments remotely.

SUBJECT OF THE INVENTION

In order to remedy the aforementioned drawbacks of the prior art, the present invention proposes a method for controlling the quality of optometric measurements for determining opto-mechanical properties and the quality of a corrective spectacle lens suitable for a spectacle wearer.

More particularly, according to the invention a method is proposed for controlling the quality of optometric measurements, which method comprises the following steps:

(a) computationally recording a first recording comprising at least one first value of a first identifier allowing a spectacle wearer to be identified and at least one other value of another identifier allowing an optometric apparatus at a first optometric measurement site to be identified;

(b) carrying out, by means of the optometric apparatus of the first site, at least one optometric measurement comprising at least one measurement of an ocular refraction parameter of the spectacle wearer and/or a measurement of horizontal and vertical positions of the pupil of the eye of this wearer relative to a frame intended to accommodate the corrective lens, the wearer being identified in the first recording;

(c) transmitting to a second site a numerical measurement dataset comprising the optometric measurement result of step (b), the numerical dataset being computationally associated with the first recording; and (d) digitally processing the optometric measurement result computationally associated with the first recording depending on numerical reference data and/or the values of the respective identifiers of the spectacle wearer and the optometric apparatus of the first recording.

Thus, an optometric measurement carried out for a wearer is identified depending on the apparatus and the optometric measurement site used thereby allowing the measurement to be traced. In addition, this optometric measurement is compared to recorded numerical reference data. The method thus allows the quality of an optometric measurement to be controlled relative to this reference data.

The following are other nonlimiting and advantageous features of the method for controlling the quality of optometric measurements according to the invention:

- step (d) comprises a step of calibrating said optometric measurement result;
- step (d) comprises the following step:
  - (d1) assigning at least one evaluation criterion to the optometric measurement result, the evaluation criterion depending on the values of the first recording; and/or
  - (d2) assigning at least one given evaluation criterion to a (database) cluster associated with a plurality of optometric apparatuses and/or a plurality of optometric measurement sites;
- the method furthermore comprises a step of transmitting the at least one evaluation criterion to the first optometric measurement site and/or to the optometric apparatus or respectively to said plurality of optometric apparatuses and/or to said plurality of optometric measurement sites;
- step (d1) or (d2) includes a step of recording the evaluation criterion in a database;
- the first computational recording is recorded in a database at the end of step (a), the numerical measurement dataset is recorded in the same database at the end of step (b) and the result of the digital processing is recorded in the same database at the end of step (d);
- step (c) of transmitting the numerical measurement dataset includes a step of recording a digital signature in the first recording of the database;
- the method furthermore comprises a step of calculating a deviation between the optometric measurement result and the numerical reference data and a step of transmitting this deviation to the first optometric measurement site and/or to the optometric apparatus;
- the numerical reference data comprise at least one evaluation criterion representative of the respect of a pre-established measurement protocol, of the reproducibility of the optometric apparatus, of the qualifications of a technician operating the optometric apparatus, of the type of optometric apparatus and/or of the complexity of the optometric measurements;
- the method furthermore comprises at least one other execution of the method of claim 1, this other execution being associated with the same first identifier value corresponding to the same spectacle wearer;
- the method furthermore comprises a step of certifying the first and/or second site depending on a digital signature assigned to the first and/or second site, respectively.

Advantageously, according to one particular embodiment, the method furthermore comprises the following steps:

(e) determining a numerical visual-correction prescription dataset of a new corrective lens (in particular the opto-mechanical properties and the quality of a corrective spectacle lens) depending on the numerical dataset of the signed measurements;

(f) having the numerical visual-correction prescription dataset digitally signed and validated by a professional qualified to prescribe the refraction powers of the new corrective lens;

(g) transmitting to a third site the numerical prescription dataset associated with the first identifier of the wearer and with a signature attached to the qualified professional; and (h) certifying the signature transmitted in the preceding step and transmitting the result of this certification to the third site.

Preferably, the method comprises the following step(s):

(i) generating at the third site a digital order dataset for the corrective lens triggering the manufacture of this eyeglass;

(j) selecting the optical design (shape and/or optical conception) or the category of the optical design or adapting the calculation of the optical design depending on the signature attached to the qualified professional;

(k) computationally recording an image file of a pre-existing visual-correction prescription of the wearer associated with the first identifier of the wearer;

(l) transmitting to the second site a numerical measurement dataset comprising the result of the measurement of step (b) and the image file of a pre-existing prescription associated with the first identifier of the wearer and with a signature attached to the first site or to the optometric apparatus;

(m) determining by processing of the image file of a pre-existing prescription the numerical visual-correction prescription dataset comprising the three refraction powers (sphere, cylinder, axis) of the new corrective lens;

(n) determining a manufacturing sequence and/or design sequence for a corrective spectacle lens suitable for the wearer depending on the value of the evaluation criterion.

DETAILED DESCRIPTION OF ONE
EXEMPLARY EMBODIMENT

The description which follows with reference to the appended drawings, which are given by way of nonlimiting examples, will make it easy to understand the essence of the invention and how it can be achieved.

Figure 2:
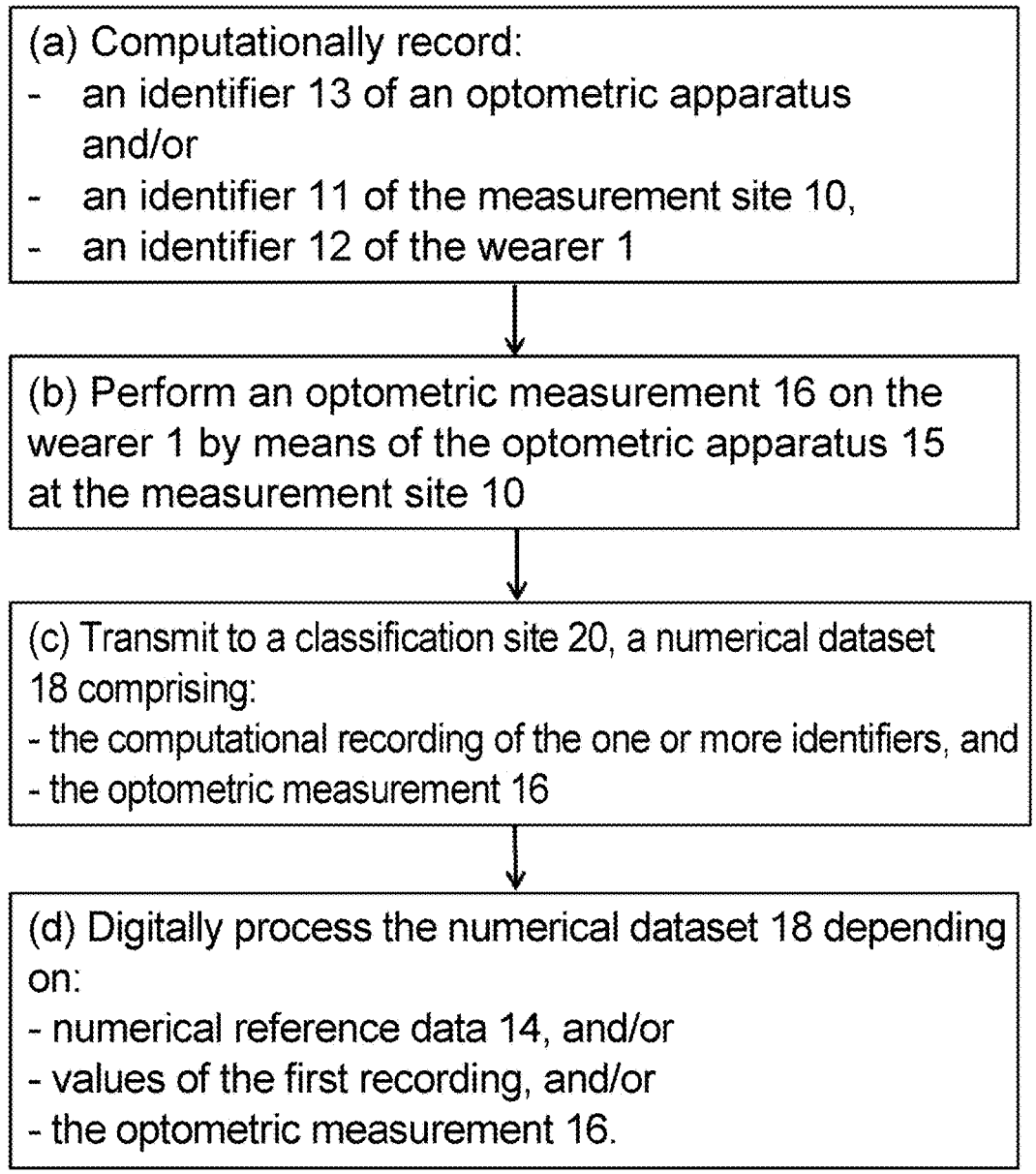
Figure 3:
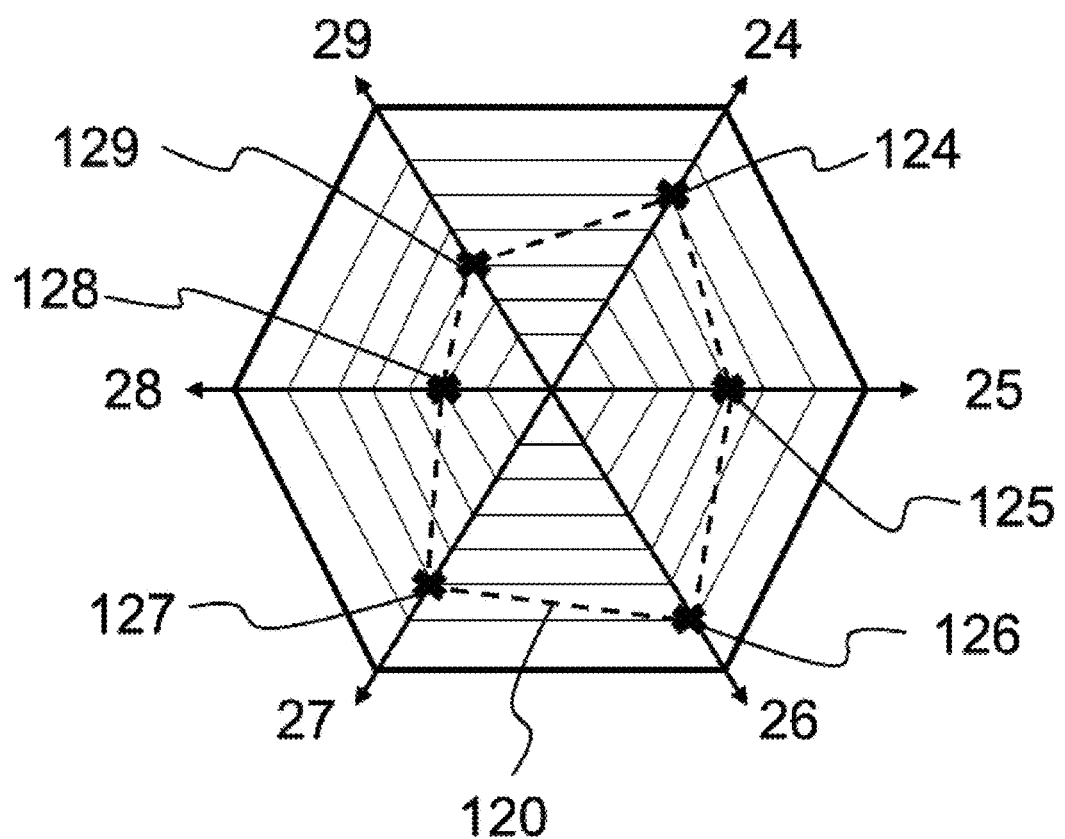

In the appended drawings:

FIG. 1 schematically shows the architecture of a system for acquiring optometric measurements, processing the optometric measurements and manufacturing ophthalmic compensation spectacles implementing the method of the invention;

FIG. 2 schematically shows a chart of steps of a method according to one embodiment of the invention; and FIG. 3 schematically shows an exemplary graphical representation of a plurality of evaluation criteria of the optometric measurements.

DEVICE

FIG. 1 schematically shows the architecture of a multi-site system for acquiring optometric measurements, processing optometric measurements, storing measurements and evaluating these measurements, and for manufacturing ophthalmic compensation spectacles.

A first optometric site 10 is the site where the optometric measurements are taken. A second site 20 is a site of processing of the optometric measurements. A third site 30 is a site of manufacture of the ophthalmic compensation spectacles. Lastly, computational storage means 40 are connected to these three sites. The first site 10 may be an eyewear retail outlet forming part of a chain of a plurality of outlets all using identical measurement methods and apparatuses, and all proposing identical ranges of frames and eyeglasses, the various sites being for example connected by a computer network.

An optometric apparatus 15 is located at the first optometric site 10. A spectacle wearer 1 is found at the optometric measuring site 10 in proximity to the optometric apparatus 15.

For example, the first optometric site 10 is an ophthalmological or optometric consultation suite or an optician's shop. Alternatively, the first optometric site 10 may correspond to a computer equipped with an image sensor. The first optometric site 10 is generally static but may also be mobile as for example in the case of a medical vehicle equipped with at least one optometric apparatus.

An optometric apparatus 15 is generally any optometric apparatus such as a refractometer, an autorefractometer, or any apparatus delivering a measurement of a geometrico-morphological parameter, such as an apparatus for measuring inter-pupillary distance, for example a pupillometer, a Visioffice- or m'eye-Fit-type measuring column or tablet, or even a simple ruler.

The optometric apparatus 15 is generally operated by an operator who may be a qualified person, an optometrist, an ophthalmologist or an optician.

A single identifier 13 is attributed to the optometric apparatus 15 of the first optometric site 10 in order to allow the optometric apparatus 15 used to be identified. Advantageously, the single identifier 13 contains information on the type of optometric apparatus, the brand of the manufacturer, the date of manufacture, the date of the last calibration, and on the type of measurements delivered by this optometric apparatus. In addition, the single identifier 13 may contain information on a quality certification of the optometric apparatus and/or of the optometric site 1. For example, a manufacturer of ophthalmic lenses or of spectacles delivers to a chain of opticians a specific optometric apparatus 15 that benefits from the certification of this manufacturer. In another example, a certificating organization is charged with controlling the conformity of the optometric apparatus 15 with a quality standard, such as for example a certification for example according to standard ISO: 10342, which relates to autorefractometers. Thus, an attestation of certification and a date of certification may be recorded in the single identifier 13 of the optometric apparatus 15. Optionally, the single identifier 13 of the optometric apparatus 15 is completed by another identifier allowing the operator who takes the measurements with this optometric apparatus 15 to be recognized.

Advantageously, another single identifier 11 is attributed to the optometric site 10 at which the optometric apparatus 15 is located. The identifier 11 may also allow a chain of eyewear retail outlets that all use the same measuring methods to be identified. Likewise, another single identifier 12 is attributed to the wearer 1.

Preferably, the various available identifiers: the identifier 13 of the optometric apparatus 15, the identifier 12 of the wearer 1, the identifier 11 of the measurement site 10 and optionally the identifier of the operator who carries out the optometric measurement, are grouped into one overall identifier 14.

The first optometric site 10 may accommodate a plurality of optometric apparatuses 15, which are either identical optometric apparatuses delivering analogous measurements or optometric apparatuses delivering complementary optometric measurements. For example, the site 10 comprises a wavefront measuring apparatus, a refractometer and an apparatus for measuring geometrico-morphological parameters of the wearer such as interpupillary distance, width of the nasal bridge, the distance between the interior face of a lens and the cornea of the eye of the wearer, and the height of the pupils relative to the lower edge of spectacles, in one or more directions of the gaze of the wearer.

The optometric apparatus generates one or more optometric measurements 16 of the spectacle wearer. The first site 10 thus delivers a numerical dataset 18 comprising on the one hand the computational recording 14 of the one or more respective identifiers 11, 12, 13 of the first site 10, of the spectacle wearer 1, and of the optometric apparatus, and on the other hand one or more optometric measurements 16. The device of the invention thus allows a plurality of numerical recordings to be generated, each numerical recording including at least one identifier 12 of the wearer and one optometric measurement 16 for one spectacle wearer 1 and optometric apparatus 15 pair.

A database of reference data 45 is preferably recorded on the computational storage means 40. The database of reference data 45 for example comprises a set of measurements carried out on an optometric apparatus 15 that is identified by its identifier 13. The database of reference data 45 may comprise a set of optometric measurements carried out by an identified operator. The database of reference data 45 may comprise a set of optometric measurements 16 associated with a wearer 1, each of these measurements 16 being associated with a measurement date and attributed to an optometric apparatus 15 identified by its identifier 13. The database of reference data 45 may also comprise optometric measurement statistics for various population categories grouped by age or various ocular pathologies.

Each numerical recording of the database relates to one pair formed from a spectacle wearer 1 and an optometric apparatus 15, which wearer and apparatus are identified by their respective identifiers. In one exemplary embodiment each numerical recording contains an optometric measurement 16, a value of the identifier of the wearer and a value of the identifier of the optometric apparatus 15. In another exemplary embodiment each numerical recording contains an optometric measurement 16 and a computational link or hyperlink linked to another register containing a value of the identifier of the wearer and a value of the identifier of the optometric apparatus 15. In yet another exemplary embodiment each numerical recording contains a first computational link to a first register containing an optometric measurement 16 and another computational link to another register containing a value of the identifier of the wearer and a value of the identifier of the optometric apparatus 15. Those skilled in the art are able to implement other adequate embodiments.

Computational means allow from each numerical recording the recorded optometric measurement and the identifier value(s) that are computationally associated therewith to be extracted.

A computational processing system 21 located at a second site 20 allows the optometric measurements 16 issued from the optometric apparatus 15 to be digitally processed. The processing system 21 is connected to the database of reference data 31. The processing system 21 processes the optometric measurements depending on data recorded in the database of reference data 31.

The processing system 21 may consist of a computer and a system for digitally processing data, which system is moreover based on known processing algorithms.

A third site 30 corresponds to a unit for manufacturing spectacles equipped with corrective lenses suitable for the sight of the wearer and to his geometrico-morphological measurements.

Advantageously, each of the measurement site 10, data processing site 20, manufacturing site 30 and computational storage site 40 is connected to the other sites by telecommunication means. The various sites are for example connected to one another by a computer network. A computational system, for example based on an exchange of tokens, makes it possible to ensure the security of the data flow communications between the various sites.

Method

FIG. 2 schematically shows an example of steps of a method for controlling the quality of optometric measurements.

In a first step a), a computational recording 14 is produced comprising at least the single identifier 13 attributed to the optometric apparatus 15 of the first optometric site 10. Complementarily, the computational recording 14 also contains the identifier 11 of the measurement site 10 and/or the identifier 12 of the wearer 1, respectively.

The computational recording 14 of the one or more identifiers 11, 12, 13 is transmitted to a database 41 of the computational means 40. Preferably, the computational recording 14 includes the attribute of a digital signature making it possible to ensure the security of the exchanges and of the recording in the database 41.

In a step b), at least one optometric measurement 16 is carried out on a spectacle wearer 1 by means of an optometric apparatus 15 of the first measurement site 10. The optometric measurement 16 for example comprises a measurement of objective ocular refraction comprising values of spherical power, cylindrical power and of axis relating to the two eyes of the wearer. Alternatively or complementarily, the optometric measurement 16 comprises a measurement of the vertical and horizontal position of the pupil of an eye of the wearer relative to a frame intended to accommodate a corrective lens.

The optometric measurement 16 may comprise a measurement for a determined posture or a plurality of measurements 161, 162 corresponding to a plurality of determined postures. For example, a first far-vision optometric measurement 161 corresponds to a posture of the wearer in which the point of fixation of the gaze has a proximity smaller than about 2 dioptres and in which the axis of the gaze is horizontal. Another near-vision optometric measurement 162 corresponds to a posture of the wearer in which the point of fixation of the gaze has a proximity comprised between about 2 and 5 dioptres and in which the axis of the gaze is inclined downward by 30 to 60° relative to a horizontal line.

Complementary information useful for the manufacture of lenses fitted in spectacles are preferably recorded and transmitted conjointly with the optometric measurement 16. Thus, the choice by the customer and/or operator of the type and quality of the ophthalmic lenses: mineral or organic material, the choice of a surface (for example antireflection) treatment, the choice of a tinted or photochromic glass, and the choice of a price range are preferably recorded in order to be transmitted not only to the manufacturing site 30 but also to the data processing site 20.

At the end of step (b), a numerical dataset 18 comprising on the one hand the computational recording 14 of the one or more identifiers 11, 12, 13 and on the other hand one or more optometric measurements 16, 161, 162 may be transmitted to the storage means 30 to be recorded in the database 41.

The numerical dataset 18 may comprise visual-correction prescription data that are not necessarily derived from the optometric measurements carried out at the measurement site 10. For example, the prescription data may be recorded from a prescription established beforehand.

Advantageously, the numerical dataset 18 and the visual-correction prescription dataset are validated and digitally signed by a professional qualified to prescribe the correction powers of the one or more new compensation lenses.

In step (c), this numerical dataset 18 comprising a computational recording 14 of the one or more identifiers 11, 12, 13 associated with one or more optometric measurements 16, 161, 162 of a wearer 1 is transmitted to the second site 20 for processing optometric measurements. Preferably, this transmitting step includes a step of recording a digital signature in the database. This is especially the case when only persons having at their disposal a digital signature are qualified to transmit numerical data 18 to a measurement site 10, to a processing site 20, to a manufacturing site 30 or to the storage means 40.

In a step (d), the numerical data 18 received by the processing site 20 are processed.

More precisely, the processing site 20 receives the numerical dataset 18 directly from the measurement site 10 or extracts the numerical dataset 18 from the computational storage means 41.

Thus, the processing system 21 accesses the numerical dataset 18 comprising at least one optometric measurement 16 associated with the computational recording 14 of the one or more identifiers, especially the identifier 13 of the optometric apparatus 15 used for the measurement, the identifier 11 of the measurement site 10 and/or the identifier 12 of the wearer 1, respectively.

The processing system 21 furthermore accesses a database of reference data 45.

Depending on the values of the computational recording 14 and the database of reference data 45, the data processing system 21 processes the optometric measurement 16. This processing may consist of one or more operations.

By way of example, the data processing comprises a step of comparing the optometric measurement with reference optometric measurements of the same type recorded in the database of reference data 45. The processing for example includes comparing the measurement 16 with a reference value corresponding to a threshold, a minimum, a maximum or an average value. Since the identifier 13 of the optometric apparatus 16, the identifier 11 of the measurement site 10 and/or the identifier 12 of the wearer 1 are known, respectively, the reference value used for the comparison may be a specific value associated with this measurement apparatus 15, with this measurement site 1 and/or with this wearer 1, respectively. It is thus possible to obtain a traceability over time of the optometric measurements relating to a measurement apparatus 15, to a measurement site 10 and/or to a wearer 1.

The data processing system may also prepare or calibrate the data in order to make it compatible with a standard framework. For example, the measurement of pantoscopic angles may differ from one apparatus to another, or from one operator to another. The processing system thus modifies the pantoscopic angle values in order that they be expressed, independently of the measurement apparatus, in one and the same measurement framework. The preparation or calibration carried out may use shifts or offsets, proportionality coefficients, or more generally any calibration relationship allowing a given measurement framework to be transposed to the standardized framework. This calibration may apply to all the measurements for which the apparatus or the operator does not provide standard values (for example pantoscopic angle, eye-glass distance (EGD) or eye rotation center (ERC) position, or face-form angle of the frame, etc.). The values thus prepared or calibrated may be transmitted to the measurement site 10 in order that the latter be able to reuse these standardized values, for example to transmit them to the manufacturing site 30.

Particularly advantageously, the processing comprises a step of evaluating a classification criterion based for example on the value of the identifier 13 of the measurement apparatus 15, of the identifier 11 of the measurement site 10 or even on an identifier attributed to the operator who performed the measurement.

For example, an optometric apparatus 15 is certified to deliver measurements with a reproducibility or a determined margin of uncertainty. A classification criterion or quality criterion or evaluation criterion may thus be attributed depending on the reproducibility of the optometric apparatus. For example, a series of measurements 16 of ocular refraction of a wearer is compared to the range of values and to the reproducibility of an optometric apparatus: if this series of measurements 16 is compatible with the range of values and reference reproducibility, an evaluation criterion may be attributed to the ocular refraction measurement 16. This evaluation criterion may be transmitted by the processing system to the measurement site. In the case where the series of measurements is validated, an average value of the series of measurements 16 of ocular refraction may then be used. A contrario, if a series of measurements 16 carried out in succession under given reproducibility conditions has a deviation larger than the reproducibility of the measurement apparatus 15 used, a value of non-validation of the measurement is generated by the processing system. Advantageously, this non-validation is transmitted to the measurement site 10. The attribution of a "non-validation" criterion makes it possible to trigger a retake of the measurement(s) or an inspection of the measurement apparatus.

In another example, a measurement 16, for example of interpupillary distance (IPD), is carried out on an optometric apparatus 15. The processing system 21 compares this IPD measurement to statistical reference values or to a preceding IPD measurement of the same wearer 1. The result of this comparison is the determination of a deviation. The value of this deviation may be transmitted to the measurement site 10. Depending on whether this deviation is smaller than or larger than a predetermined threshold, the processing system 21 transmits to the measurement site 10 a criterion of validation or non-validation of the measurement 16, which may thus be reiterated.

In certain cases, the apparatus or operator may not be certified to deliver measurements with a certain reproducibility or margin of uncertainty, for example if it is a question of an unknown or new apparatus.

The delivery of the measurements of the apparatus may then be compared with a minimum acceptable threshold, and thus it is possible to verify whether the measurement performance is sufficient to accept the measurements, and to return to the site 10 information on the acceptability of these measurements.

Depending on the presence or absence of a quality certificate attributed to an optometric apparatus, the processing system attributes a quality criterion to the optometric measurement.

In the present document, by associate or attribute what is meant is the action of creating a computational link between computational data. This computational link may be a common recording in a given database, or a computational link between distinct recordings in one or more databases. A value associated or attributed to a recording is therefore computationally connected unequivocally to this recording.

Another evaluation criterion may be based on the respect of a pre-established measurement protocol. For example, a quality charter applying to a measurement apparatus 16 defines the steps of a measurement protocol, the measurement conditions, adjustments and/or the order of execution of the various steps (far-vision measurement, near-vision measurement, etc.) which are necessary to obtain measurements according to a standard. The recording of the measurements makes it possible to verify the order in which the measurement steps were carried out and for each step whether the defined execution conditions were respected. An evaluation criterion of a pre-established measurement protocol may thus be assigned a posteriori to a measurement 16 or to a set of optometric measurements. The processing may make it possible to check the conformity of the measurements carried out with a predefined measurement protocol.

In yet another example, the evaluation criterion attributed to the measurement 16 is based on the professional qualifications of the operator who carried out the measurement. For example, if the measurement is carried out by a highly qualified person, a high confidence criterion may be attributed to this measurement 16. A contrario, in the case where the wearer carried out an IPT measurement himself by way of a computer video camera, a low confidence criterion is attributed to this measurement. This criterion and the reason explaining the low value of the criterion (repeatability problem, insufficient precision, insufficient dynamic range, etc.) may be returned to the site 10. By feedback, the site 10 may optionally determine corrective means in order to achieve a higher criterion.

An evaluation criterion may also be associated with the degree of complexity of the measurements required to deliver a suitable spectacle proposition.

An additional criterion for example corresponds to the number of returns due to fitting or centering errors or due to the spectacles not being suitable for the sight of the wearer. This additional criterion may be assigned a weighting factor in order to be combined with a suitable spectacle proposition function or a suitable spectacle type decision function.

It is possible to create a cluster in the database corresponding to a group of pieces of optometric equipment and/or a group of measurements, these groups being associated for example with a group of optician's shops. Thus, it is possible to assign to this (corresponding) cluster a given return criterion, or equipment malfunction criterion and/or measurement protocol failure criterion. This return or failure criterion may be simultaneously assigned to a cluster corresponding to a plurality of nonconforming or failed pieces of equipment and/or measuring methods.

Lastly, another evaluation criterion may be associated with the identifier 11 of a determined measurement site 10, for example depending on the quality of the available optometric apparatuses or the history of measurements carried out at this measurement site 10. The identifier 11 of the measurement site 10 may allow members of a professional network of ophthalmic compensation spectacle distributors to be identified. This network is equipped with a particular category of optometric apparatuses, which is thus automatically recognized. Let us take the case of a network of professionals that distributes exclusively for one manufacturer a certain quality of ophthalmic lenses, for example progressive or multifocal lenses. Depending on the identifier 11 of the measurement site, various eyeglass catalogues are then made accessible for manufacturing and distribution by the identified measurement site 10.

The evaluation criterion may be a binary criterion. Thus, a binary evaluation criterion corresponds to the availability or not of an optometric measurement, such as an IPD measurement, or even a near-vision and far-vision differentiated refraction measurement. A binary evaluation criterion may also correspond to the validation or non-validation of an optometric measurement. Another type of evaluation criterion may take a plurality of values on a scale.

The value of the evaluation criterion may then be transmitted to the storage system 40 to enrich a statistical database and/or to the measurement site 10. Thus, the evaluation criterion may allow an ocular refraction measurement or a measurement of a geometrico-morphological parameter to be validated or not.

The processing of a measurement 16 may also be associated with a plurality of evaluation criteria such as the criteria detailed above.

These various evaluation criteria are for example represented on a radar chart, such as that in FIG. 3, in which each radius of the radar represents the graduated scale of an evaluation criterion. The number of radii corresponds to the number of evaluation criteria.

Each evaluation criterion may be associated with one specific measurement: for example a first criterion 24 is associated with the ocular refraction measurement of the right eye of the wearer 1, a second criterion 25 is associated with the ocular refraction measurement of the left eye, a third criterion 26 is associated with the respect of a measurement protocol applied to the refractometry apparatus, a fourth criterion 27 is associated with a measurement of interpupillary deviation of the wearer, a fifth criterion 28 is associated with the quality of a measurement of a right visual axis height relative to the lower edge of a frame, and a sixth criterion 29 is associated with the quality of a measurement of a left visual axis height relative to the lower edge of a frame.

Alternatively, one and the same measurement may be associated with a plurality of evaluation criteria such as: the reproducibility of this measurement, the respect of the measurement protocol, the deviation relative to a prior measurement of the same wearer, etc.

The value of each evaluation criterion is represented by a mark on the corresponding radius. Such a chart makes it possible to visualize an average value or threshold, minimum or maximum values for each of the evaluation criteria.

In the case where a plurality of evaluation criteria are calculated, a weighting coefficient is advantageously assigned to each evaluation criterion.

A multi-criteria evaluation makes possible an overall comparison of the evaluation of the measurements with pre-established standard reference measurements. It is possible for example to calculate an area of a spider chart, the area being dependent on an overall quality of the measurements. The results of the mono- or multi-criteria evaluation are transmitted to the manufacturing site 30. These results are also transmitted to the storage means 30, for the purpose of traceability of the measurements or to complete a statistical database.

Depending both on the optometric measurements and the result of the evaluation of these optometric measurements, the manufacturer may determine a manufacturing sequence and/or a design sequence that is the most suitable for the needs of the wearer. Preferably, domains defined by limiting values are recorded for one or more evaluation criteria. These domains are associated computationally with various corrective spectacle lens manufacturing sequences and/or design sequences of a manufacturer.

For example, for a given ocular correction prescription associated with a measurement evaluation of average quality, the manufacturer proposes eyeglasses in an average quality range and/or in a predefined design category compatible with the required prescription. For example, it is possible to choose a personalized progressive design or a generic progressive design, or a progressive design associated with the activity of the wearer, or a particular type of eyeglass (SV/DBF/PAL).

In the case of an ophthalmic correction prescription associated with a measurement evaluation of excellent quality, the manufacturer may propose personalized eyeglasses having extremely precise characteristics and/or in a top-of-the-range design category. In this case, the manufacturer may propose progressive eyeglasses the positions of the focal points of which are determined very precisely.

Conversely, for a given ocular correction prescription that is associated with optometric measurements evaluated with a low degree of quality, it is preferable to orient the manufacture toward corrective eyeglasses having high parameterization tolerances, which are compatible with the margins of error associated with the low quality of the optometric measurements.

The manufacturing site 30 thus defines a proposition of spectacles equipped with eyeglasses compatible with the optometric measurements, which may then be transmitted from the manufacturing site 30 to the measurement site 10. The optician or the operator of the measurement site 10 may thus propose to the wearer one or more pairs of spectacles compatible with the measurements carried out and with the manufacturing constraints.

After validation of the choice of spectacles by the wearer, the manufacturer of the spectacles may be triggered.

The manufacturing sequence of the eyeglasses is preferably recorded on the computational storage means 30.

This method thus allows the manufacture of the spectacles to be tailored not only depending on the required correction, but also depending on an evaluation of the quality of the optometric measurements carried out to adjust the compensation eyeglasses to the chosen spectacle frame.

The invention claimed is:

1. A method for controlling the quality of optometric measurements for determining the optical-mechanical properties and the quality of a corrective spectacle lens suitable for a spectacle wearer, the controlling method comprising the following steps:
  (a) computationally recording a first recording comprising at least one first value of a first identifier allowing a spectacle wearer to be identified and at least one other value of another identifier allowing an optometric apparatus at a first optometric measurement site to be identified;
  (b) carrying out, by means of the optometric apparatus of the first site, at least one optometric measurement comprising at least one measurement of an ocular refraction parameter of at least one eye of the spectacle wearer and/or a measurement of horizontal and vertical positions of the pupil of the eye of this wearer relative to a frame intended to accommodate the corrective lens;
  (c) transmitting to a second site a numerical measurement dataset comprising the optometric measurement result of step (b), the numerical dataset being computationally associated with the first recording; and
  (d) digitally processing the optometric measurement result computationally associated with the first recording depending on numerical reference data and/or the respective identifier of the optometric apparatus of the first recording;
  (e) determining a numerical visual-correction prescription dataset of a new corrective lens depending on the numerical dataset computationally associated with the first recording;
  (f) having the numerical visual-correction prescription dataset digitally signed and validated by a professional qualified to prescribe the refraction powers of a new corrective lens;
  (g) transmitting to a third site the numerical prescription dataset associated with the first identifier of the wearer and with a signature attached to the qualified professional;
  (h) certifying the signature transmitted in step (g) and transmitting the result of this certification to the third site;
  (i) generating at the third site a digital corrective-lens order dataset triggering the manufacture of this eyeglass;
  (j) selecting an optical design or a category of optical design or adapting the calculation of the design depending on the signature attached to the qualified professional;
  (k) computationally recording an image file of a pre-existing visual-correction prescription of the wearer associated with the first identifier of the wearer;
  (l) transmitting to the second site a numerical measurement dataset comprising the result of the measurement of step (b) and the image file of a pre-existing prescription, which are associated with the first identifier of the wearer and with a digital signature attached to the first site or to the optometric apparatus; and
  (m) determining by processing of the image file of a pre-existing prescription and by processing the optometric measurement of step (b) computationally associated with the first recording a numerical visual-correction prescription dataset wherein the prescription dataset comprises three refraction powers of the new corrective lens.

2. The method as claimed in claim 1, wherein step (d) comprises a step of calibrating said optometric measurement result.

3. The method as claimed in claim 1, wherein step (d) comprises the following step:
  (d1) assigning at least one evaluation criterion to the optometric measurement result, the evaluation criterion depending on the respective identifier of the optometric apparatus of the first recording.

4. The method as claimed in claim 1, wherein step (d) comprises the following step:
  (d1) assigning at least one given evaluation criterion to a cluster associated with a plurality of optometric apparatuses and/or a plurality of optometric measurement sites.

5. The method as claimed in claim 4, furthermore comprising a step of transmitting the at least one evaluation criterion to the first optometric measurement site and/or to the optometric apparatus or respectively to said plurality of optometric apparatuses and/or to said plurality of optometric measurement sites.

6. The method as claimed in claim 3, wherein step (d) includes a step of recording the evaluation criterion in a database.

7. The method as claimed in claim 1, wherein the first recording is recorded in a database at the end of step (a), a numerical measurement of the at least one optometric measurement is determined at step (b) and is recorded in the same database at the end of step (b) and the result of the digital processing is recorded in the same database at the end of step (d).

8. The method as claimed in claim 6, wherein step (c) of transmitting the numerical measurement dataset includes a step of recording a digital signature in the first recording of the database.

9. The method as claimed in claim 1, further comprising:
  a step of analyzing the digitally processed measurement result in association with numerical reference data, and
  a step of calculating a deviation between the optometric measurement result and the numerical reference data and a step of transmitting this deviation to the first optometric measurement site and/or to the optometric apparatus.

10. The method as claimed in claim 1, further comprising a step of analyzing the digitally processed measurement result in association with numerical reference data, wherein the numerical reference data comprise at least one evaluation criterion representative selected from the group of: the respect of a pre-established measurement protocol, the reproducibility of the optometric apparatus, the qualifications of a technician operating the optometric apparatus, the type of optometric apparatus and the complexity of the optometric measurements.

11. The method as claimed in claim 1, furthermore comprising at least one other execution of the complete method of claim 1, this other execution being associated with the same first identifier value corresponding to the same spectacle wearer.

12. The method as claimed in claim 1, further comprising a step of assigning a digital signature to the first and/or to the second site, and further certifying the first and/or the second site depending on the digital signature assigned to the first and/or the second site, respectively.

13. The method as claimed in claim 7, wherein step (c) of transmitting the numerical measurement dataset includes a step of recording a digital signature in the first recording of the database.

14. The method as claimed in claim 3, wherein step (d) comprises the following step:
  (d2) assigning at least one given evaluation criterion to a cluster associated with a plurality of optometric apparatuses and/or a plurality of optometric measurement sites.

15. The method as claimed in claim 14, wherein step (d) includes a step of recording the evaluation criterion in a database.

16. The method as claimed in claim 15, wherein the first recording is recorded in a database at the end of step (a), a numerical measurement of the at least one optometric measurement is determined at step (b) and is recorded in the same database at the end of step (b) and the result of the digital processing is recorded in the same database at the end of step (d).

* * * * *